US012622734B2

(12) United States Patent
Lashure et al.

(10) Patent No.: US 12,622,734 B2
(45) Date of Patent: May 12, 2026

(54) OFFSET ACETABULAR SHELL IMPACTOR ADAPTER

(71) Applicant: DEPUY SYNTHES PRODUCTS, INC., Raynham, MA (US)

(72) Inventors: Daniel E. Lashure, Fort Wayne, IN (US); Cory A. Shulaw, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 0 days.

(21) Appl. No.: 18/746,519

(22) Filed: Jun. 18, 2024

(65) Prior Publication Data

US 2024/0415557 A1     Dec. 19, 2024

Related U.S. Application Data

(62) Division of application No. 17/314,404, filed on May 7, 2021, now Pat. No. 12,011,203.

(51) Int. Cl.
| | |
|---|---|
| *A61F 2/46* | (2006.01) |
| *A61B 17/92* | (2006.01) |
| *A61B 17/00* | (2006.01) |

(52) U.S. Cl.
CPC ............ *A61B 17/92* (2013.01); *A61F 2/4609* (2013.01); *A61B 2017/00367* (2013.01); *A61B 2017/925* (2013.01)

(58) Field of Classification Search
CPC ................. A61F 2/4607; A61F 2/4609; A61F 2002/4681
See application file for complete search history.

(56) References Cited

U.S. PATENT DOCUMENTS

| | | | |
|---|---|---|---|
| 8,393,409 | B2 | 3/2013 | Pedicini |
| 8,602,124 | B2 | 12/2013 | Pedicini |
| 8,695,726 | B2 | 4/2014 | Pedicini |
| 8,936,105 | B2 | 1/2015 | Pedicini |
| 8,936,106 | B2 | 1/2015 | Pedicini |
| 9,901,354 | B2 | 2/2018 | Pedicini |
| RE46,954 | E | 7/2018 | Pedicini |
| RE46,979 | E | 8/2018 | Pedicini |
| 10,342,591 | B2 | 7/2019 | Pedicini |
| 10,381,696 | B2 | 8/2019 | Pedicini |
| 10,420,567 | B2 | 9/2019 | Pedicini |
| 10,446,895 | B2 | 10/2019 | Pedicini |
| 10,603,050 | B2 | 3/2020 | Pedicini |
| RE47,963 | E | 4/2020 | Pedicini |
| RE47,997 | E | 5/2020 | Pedicini |
| RE48,184 | E | 9/2020 | Pedicini |

(Continued)

OTHER PUBLICATIONS

PCT International Search Report for International Application No. PCT/IB2022/053818, Jul. 21, 2022, 7 pages.

*Primary Examiner* — David W Bates
(74) *Attorney, Agent, or Firm* — Barnes & Thornburg LLP

(57) ABSTRACT

An orthopaedic surgical instrument may include an elongated body with an implant end and an impactor end. A latch lever may be pivotally coupled to the elongated body. The latch lever may be moveable between an open position and a latched position in which the latch lever is retained within the body. An acetabular shell component may be rigidly attached to the implant end of the elongated body. An automated surgical impactor may be attached to the impactor end.

6 Claims, 10 Drawing Sheets

(56)                    References Cited

U.S. PATENT DOCUMENTS

| | | | |
|---|---|---|---|
| RE48,251 E | 10/2020 | Pedicini | |
| RE48,387 E | 1/2021 | Pedicini | |
| RE48,388 E | 1/2021 | Pedicini | |
| 10,912,597 B2 | 2/2021 | Pedicini | |
| 2007/0173856 A1 | 7/2007 | Parker | |
| 2008/0221576 A1* | 9/2008 | Keller | A61F 2/4607 |
| | | | 606/151 |
| 2013/0226186 A1 | 8/2013 | Burgi | |
| 2015/0182351 A1* | 7/2015 | Behzadi | A61B 17/92 |
| | | | 606/91 |
| 2016/0135963 A1 | 5/2016 | Kerboul et al. | |
| 2016/0213492 A1 | 7/2016 | Castello et al. | |
| 2017/0027715 A1 | 2/2017 | Huang | |
| 2017/0304078 A1* | 10/2017 | Chenaux | A61F 2/4609 |
| 2018/0055552 A1 | 3/2018 | Pedicini | |
| 2018/0055553 A1 | 3/2018 | Pedicini | |
| 2018/0055554 A1 | 3/2018 | Pedicini | |
| 2018/0338751 A1 | 11/2018 | Pedicini | |
| 2019/0183554 A1 | 6/2019 | Pedicini | |
| 2019/0223889 A1 | 7/2019 | Pedicini | |
| 2019/0282286 A1 | 9/2019 | Pedicini | |
| 2019/0305394 A1 | 10/2019 | Pedicini | |
| 2020/0197028 A1 | 6/2020 | Pedicini | |

* cited by examiner

OFFSET ACETABULAR SHELL IMPACTOR ADAPTER

This application is a divisional application and claims priority to U.S. patent application Ser. No. 17/314,404, now U.S. Pat. No. 12,011,203, which was filed on May 7, 2021, the entirety of the above-identified application is hereby incorporated by reference.

TECHNICAL FIELD

The present disclosure relates generally to orthopaedic instruments for use in the performance of an orthopaedic joint replacement procedure, and more particularly to orthopaedic surgical instruments for use in the performance of a hip replacement procedure.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral head prosthetic component. An acetabular prosthetic component generally includes an outer shell configured to engage the acetabulum of the patient and an inner bearing or liner coupled to the shell and configured to engage the femoral head. The femoral head prosthetic component and inner liner of the acetabular component form a ball and socket joint that approximates the natural hip joint.

Typical joint arthroplasty surgical procedures include impaction of surgical instruments (e.g., broaches, chisels, or other cutting tools) and/or prosthetic implants into the patient's bone. Historically, impaction has been performed by an orthopaedic surgeon manually striking a surgical instrument using a surgical mallet or hammer. Such manual impaction can be unpredictable and imprecise. Additionally, typical manual impaction instruments may require the surgeon to hold the instrument with one hand and strike the instrument with a mallet held in the surgeon's other hand.

Certain automated surgical impactors are capable of performing a series of percussive impacts that each provide a controlled amount of impaction energy. An automated surgical impactor may be used with one or more adapters to connect to various surgical instruments and/or implants. Typical adaptors connect to the surgical instrument and/or implant using a rigid drive train including one or more drive shafts, gear trains, or other rigid mechanical connections.

SUMMARY

According to one aspect, an orthopaedic surgical instrument includes an elongated body extending from a first end to a second end, a slideable bolt, a carrier slideably coupled to the elongated body, an elongated lever that extends from a pivot end to a latch end, a leaf spring, and a pushbutton catch coupled to the elongated body. The first end of the elongated body is configured to be received by an automated surgical impactor. The slideable bolt includes a head and a threaded body positioned at the second end of the elongated body. The threaded body extends outward from the second end of the elongated body. A notch defined in the carrier engages the head of the slideable bolt. The pivot end of the elongated lever is pivotally coupled to the elongated body.

The leaf spring has a first end that is pivotally coupled to the lever and a second end that is pivotally coupled to the carrier such that movement of the lever causes movement of the carrier. The lever is movable between a first position in which the latch end is spaced apart from the elongated body and a second position in which the latch end is captured by the pushbutton catch. In the second position the leaf spring urges the carrier inward away from the implant end, and in the second position the carrier pulls the head of the bolt inward away from the implant end.

In an embodiment, the elongated body includes a straight segment, an angled segment, and an offset segment. The straight segment extends from the first end to the angled segment, the angled segment extends from the straight segment to the offset segment, and the offset segment extends from the angled segment to the second end. In an embodiment, a centerline of the first end is offset by a predetermined distance from a center of the slideable bolt. In an embodiment, the predetermined distance is 41 millimeters.

In an embodiment, the elongated body includes a top surface having an elongated opening defined therein, a bottom surface opposite the top surface and having an elongated opening defined therein, one or more inner walls extending between the elongated opening defined in the top surface and the elongated opening defined in the bottom surface, and a first cavity defined by the one or more inner walls. The pivot end of the elongated lever is pivotally coupled to the elongated body within the first cavity, and the latch end of the elongated lever extends out of the first cavity through the elongated opening defined in the top surface. The leaf spring is positioned within the first cavity. When the elongated lever is in the second position the carrier pulls the head of the bolt inward toward the first cavity.

In an embodiment, the elongated body includes a convex front surface positioned on the second end of the elongated body. A circular aperture is defined in the convex front surface, and the circular aperture opens into the first cavity. The threaded body of the slideable bolt extends outward from the second end through the circular aperture.

In an embodiment, the elongated body includes a first cross member positioned within the first cavity and coupled between the inner walls. A top surface of the first cross member defines a guideway to the head of the slideable bolt, wherein the guideway is in communication with the first cavity. In an embodiment, the orthopaedic surgical instrument further includes a second spring coupled between the elongated lever and the elongated body. The second spring biases the elongated lever in the first position. In an embodiment, the elongated body includes a second cross member positioned within the first cavity and coupled between the inner walls. The second spring is positioned between the pivot end of the lever and a bottom surface of the second cross member. In an embodiment, the elongated lever includes a stop extending outward from a top surface of the elongated lever. When the elongated lever is in the first position the stop contacts the bottom surface of the second cross member.

In an embodiment, the carrier includes an elongated body having a rail that surrounds a front and sides of the carrier. An elongated aperture is defined in the bottom surface of the elongated body, the elongated aperture extending from the elongated opening in the bottom surface toward the second end. An inner wall extends inward from the elongated opening into the first cavity, and a groove is defined in the inner wall surrounding the elongated aperture. The rail of the carrier is positioned in the groove.

In an embodiment, the elongated body includes a first side wall and a second side wall opposite the first side wall, an opening defined in the first side wall, one or more inner walls extending inwardly from the opening in the first side wall, wherein the one or more inner walls define a second cavity, and a second opening defined in the top surface between the first end and the elongated opening, wherein the second opening opens into the second cavity. The pushbutton catch is positioned in the second cavity. When the elongated lever is in the second position, a latch extending downward from the latch ending is positioned in the second cavity and retained by the pushbutton catch. In an embodiment, the pushbutton catch is moveable between a first position in which the pushbutton catch engages the latch positioned within the second cavity and a second position in which the pushbutton catch does not engage the latch. In an embodiment, the orthopaedic surgical instrument further includes a second spring positioned in the second cavity. The second spring is configured to bias the pushbutton catch in the first position.

In an embodiment, the pushbutton catch includes a button surface positioned toward the first side wall of the elongated body, a pair of side walls extending from the button surface into the second cavity, a back wall that connects the pair of side walls, and a catch that extends from the back wall into the second cavity. In an embodiment, the latch of the elongated lever includes a first cam surface, and the catch of the pushbutton catch includes a second cam surface. When the elongated lever is moved from the first position to the second position, the first cam surface engages the second cam surface. When the first cam surface engages the second cam surface, the pushbutton catch is urged from the first position to the second position.

According to another aspect, a method for performing an orthopaedic surgical procedure includes securing an acetabular shell component to a first end of an orthopaedic surgical instrument; moving a lever of the orthopaedic surgical instrument from a first position to a second position in response to securing the acetabular shell component to the first end, wherein moving the lever from the first position to the second position comprises latching the lever in the second position and applying tension with a compliant member of the orthopaedic surgical instrument on the acetabular shell component against the first end; and coupling a second end of the orthopaedic surgical instrument to an automated surgical impactor in response to moving the lever.

In an embodiment, securing the acetabular shell component to the first end comprises threading a central threaded hole of the acetabular shell component onto a threaded body of a slideable bolt of the orthopaedic surgical instrument, wherein the threaded body extends outward from the first end of the orthopaedic surgical instrument; positioning a driver tool in a guideway defined by a top surface of the orthopaedic surgical instrument in response to threading the central threaded hole onto the threaded body; and tightening a head of the slideable bolt with the driver tool in response to positioning the driver tool.

In an embodiment, the method further includes adjusting a rotational position of the acetabular shell component in response to securing the acetabular shell component to the first end; wherein moving the lever further comprises moving the lever in response to adjusting the rotational position.

In an embodiment, the method further includes impacting the acetabular shell component with the automated surgical impactor into a surgically prepared acetabulum of a patient in response to coupling the second end to the automated surgical impactor; depressing a pushbutton catch of the orthopaedic surgical instrument in response to impacting the acetabular shell component, wherein depressing the pushbutton catch comprises unlatching the lever from the second position and releasing tension with the compliant member; and releasing the acetabular shell component from the first end of the orthopaedic surgical instrument in response to depressing the pushbutton catch.

BRIEF DESCRIPTION OF THE DRAWINGS

The detailed description particularly refers to the following figures, in which.

DETAILED DESCRIPTION OF THE DRAWINGS

Figure 1:
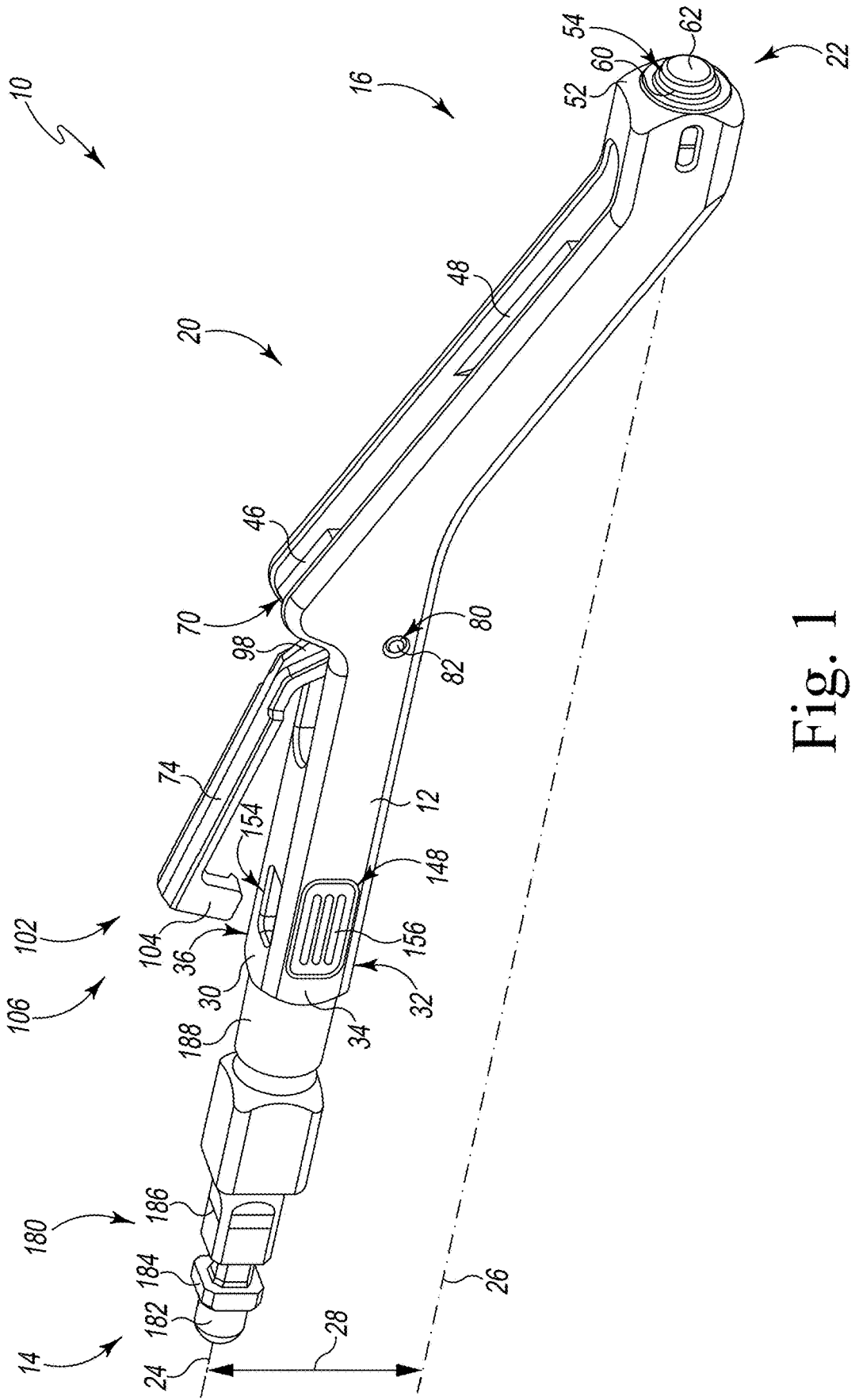
FIG. 1 is a perspective view of an offset acetabular shell impactor adapter in an open configuration.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. Additionally, it is to be understood that terms such as top, bottom, front, rear, side, height, length, width, upper, lower, and the like that may be used herein merely describe points of reference and do not necessarily limit embodiments of the present disclosure to any particular orientation or configuration.

Referring now to FIGS. 1-5, an offset acetabular shell impactor adapter 10 (hereinafter impactor adapter 10) is shown. The impactor adapter 10 is an orthopaedic surgical instrument; that is, a surgical tool used by a surgeon in performing an orthopaedic surgical procedure. As such, it should be appreciated that, as used herein, the terms "orthopaedic surgical instrument" and "orthopaedic surgical instruments" are distinct from orthopaedic implants or prostheses that are surgically implanted in the body of the patient. As described further below, the impactor adapter 10 may be used with an automated surgical impactor to seat an acetabular shell component into a patient's surgically prepared acetabulum.

As shown in FIGS. 1-5, the impactor adapter 10 includes an elongated, offset body 12 extending from an impactor attachment end 14 to an implant end 16. As described further below, in use the impactor end 14, also called the distal end or the rear end, may be attached to an automated surgical impactor tool. Similarly, in use, the implant end 16, also called the proximal end, the tip end, or the front end, may be attached to an acetabular shell component or other prosthetic implant.

In the illustrative embodiment, the body 12 is formed from a metallic material, such as, for example, stainless steel or cobalt chromium. The elongated body 12 includes a straight segment 18 positioned at the impactor end 14, an angled segment 20, and an offset segment 22 positioned at the implant end 16. The straight segment 18 defines a straight segment axis 24 and the offset segment 22 defines an offset segment axis 26. The angled segment 20 extends such that the axes 24, 26 are offset by a distance 28, which is illustratively 41 millimeters. The illustrative offset, elongated body 12 may be used with a direct anterior approach (DAA) surgical procedure for performing hip arthroplasty.

Each of the segments 18, 20, 22 are generally rectangular in cross section and thus have a top surface 30 and a bottom surface 32 positioned opposite the top surface 30, as well as a pair of side surfaces 34, 36. A pair of elongated openings 38, 40 are defined in each of the top surface 30 and the bottom surface 32, respectively. One or more inner walls 42 extend between the openings 38, 40 through the body 12 and define a cavity 44 inside the body 12. A top cross member 46 and a middle cross member 48 are positioned within the cavity 44 between the inner walls 42. Each cross member 46, 48 has a curved upper surface 50.

The implant end 16 includes a convex surface 52 with a central circular aperture 54 defined thereon. An inner wall 56 extends inward from the central circular aperture 54, defining a passageway 58 that extends into the interior cavity 44. A boss 60 surrounds the circular aperture 54 and extends outward from the convex surface 52.

Figure 2:
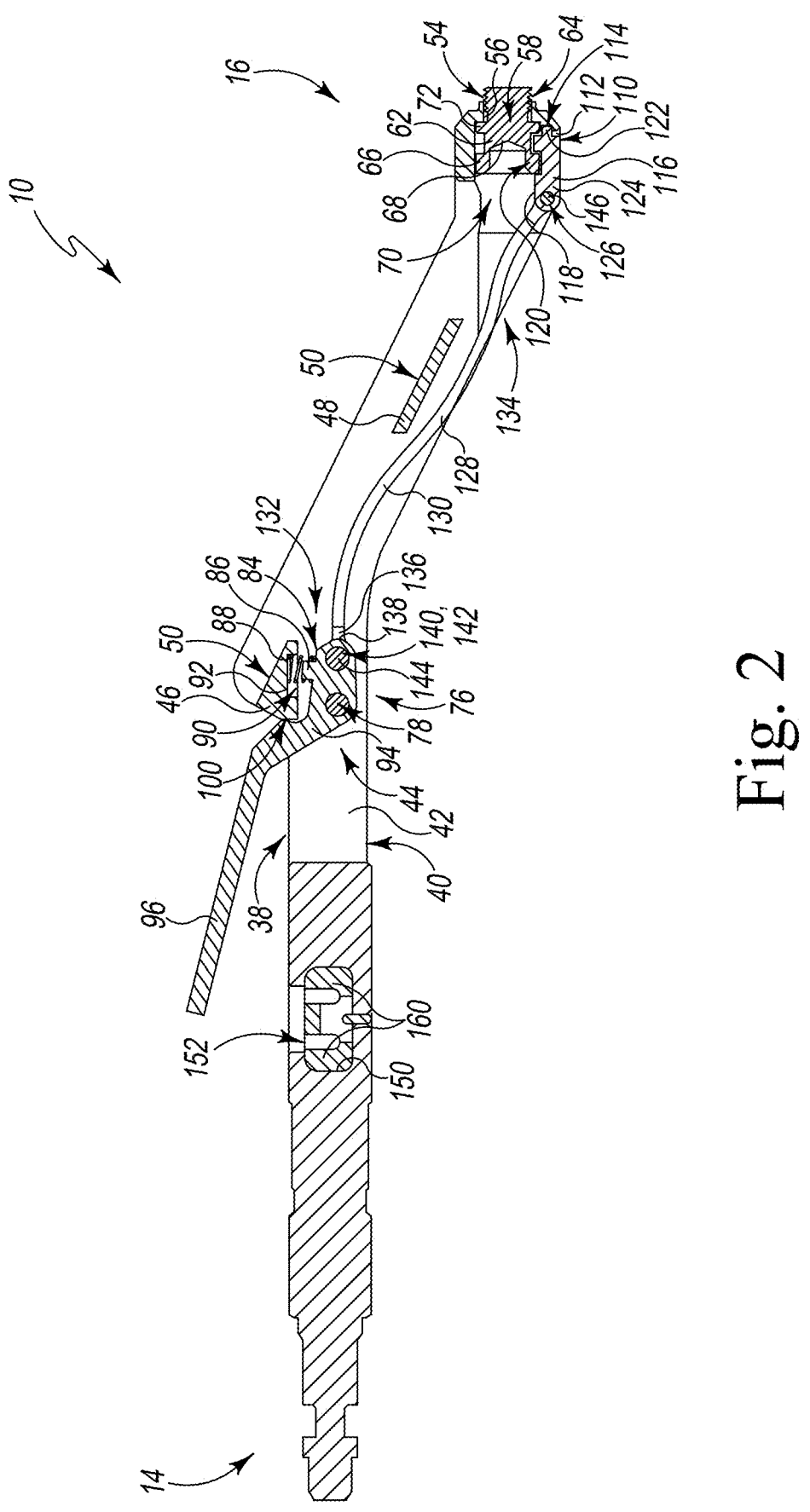
FIG. 2 is a cross-sectional elevation view of the offset acetabular shell impactor adapter of FIG. 1.
Figure 4:
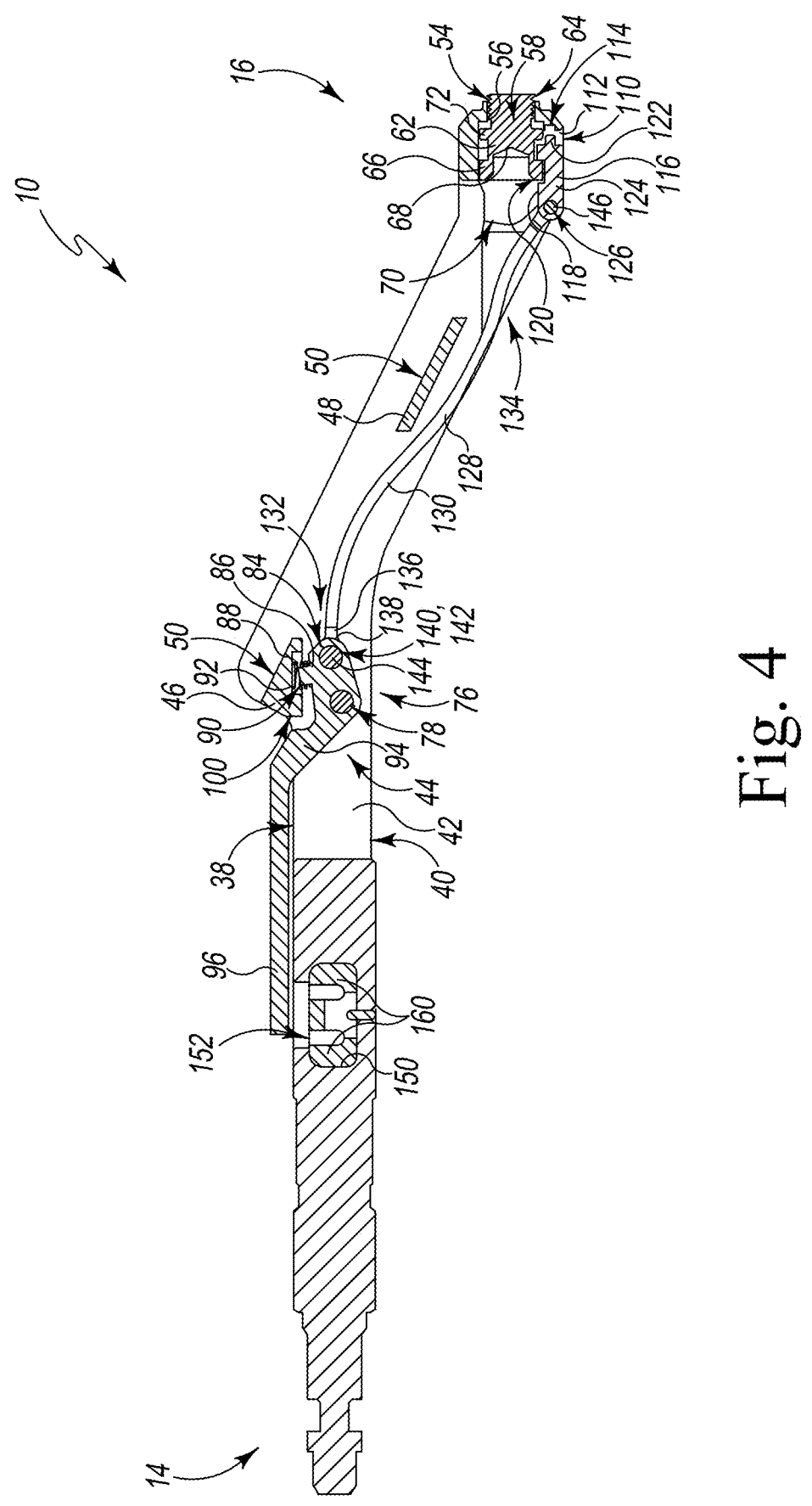
FIG. 4 is a cross-sectional elevation view of the offset acetabular shell impactor adapter of FIG. 3.

As shown in the cross-sectional views of FIGS. 2 and 4, a slideable bolt 62 is positioned in the circular aperture 54. The bolt 62 includes a threaded body 64 and a head 66. The head 66 includes a top surface 68 that defines a pocket configured to receive a fastening tool. Illustratively, the top surface 68 includes a hex shape configured to receive a manual ball-end hex driver; however, in other embodiments the bolt 62 may be configured to receive any other suitable screwdriver or fastening tool. The curved upper surfaces 50 of the cross members 46, 48 and the inner walls 42 of the body 12 cooperate to define a guideway 70 that leads to the pocket defined in the top surface 68 of the bolt 62. The threaded body 64 extends outward from the implant end 16 through the circular aperture 54, and the bolt 62 is slideable inward and outward relative to the implant end 16. A collar 72 surrounds the bolt 62. The collar 72 has a larger diameter than the circular aperture 54, thereby retaining the bolt 62 within the body 12.

Referring again to FIGS. 1-5, the impactor adapter 10 includes an elongated latch lever 74 that extends outward from the cavity 44 through the opening 38 formed in the top surface 30. The latch lever 74 includes a pivot end 76 that is pivotally mounted to the body 12 within the cavity 44. Illustratively, a bore 78 is defined through the pivot end 76, and a pair of circular openings 80 are defined through the side surfaces 34, 36 of the body 12. The bore 78 encompasses the pivot point of the latch lever 74. A pin 82 is positioned in the bore 78 and the openings 80 such that the latch lever 74 is joined with the body 12 and allowed to rotate about the pin 82. In the illustrative embodiment, the pin 82 is press-fit into the openings 80; however, any suitable method of securing the pin 82 may be used.

The pivot end 76 further includes an upper surface 84 having a pin 86 extending outward from the upper surface 84. The pin 86 is captured within a helical spring 88. The spring 88 is itself retained within a pocket 90 defined in a lower surface 92 of the top cross member 46. The spring 88 urges against the lower surface 92 and the upper surface 84, which biases the latch lever 74 toward an open position as shown in FIGS. 1-2.

The latch lever 74 further includes a neck 94 extending from the pivot end 76 toward a lever body 96. A top fin 98 extends outward from the neck 94. As the lever 74 reaches the fully open position, the fin 98 contacts a back surface 100 of top cross member 46. Thus, the fin 98 operates as a stop that limits range of motion for the lever 74. The throw of the lever 74, that is, the angle between the body 96 of the lever 74 and the straight segment 18 of the body 12 when the lever 74 is in the fully open position, may be limited to less than about 40-45 degrees.

Figure 3:
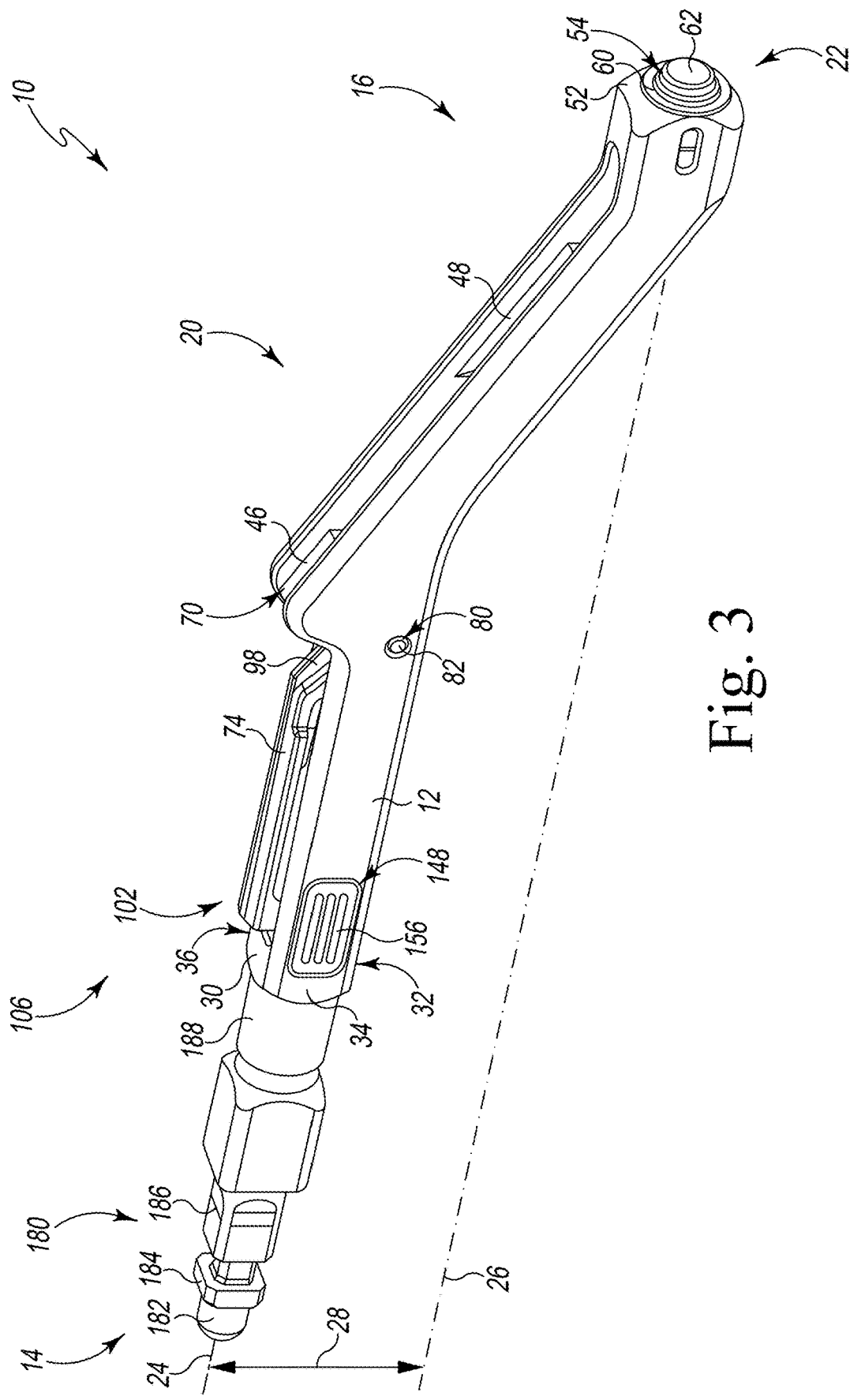
FIG. 3 is a perspective view of the offset acetabular shell impactor adapter of FIG. 1 in a latched configuration.
Figure 5:
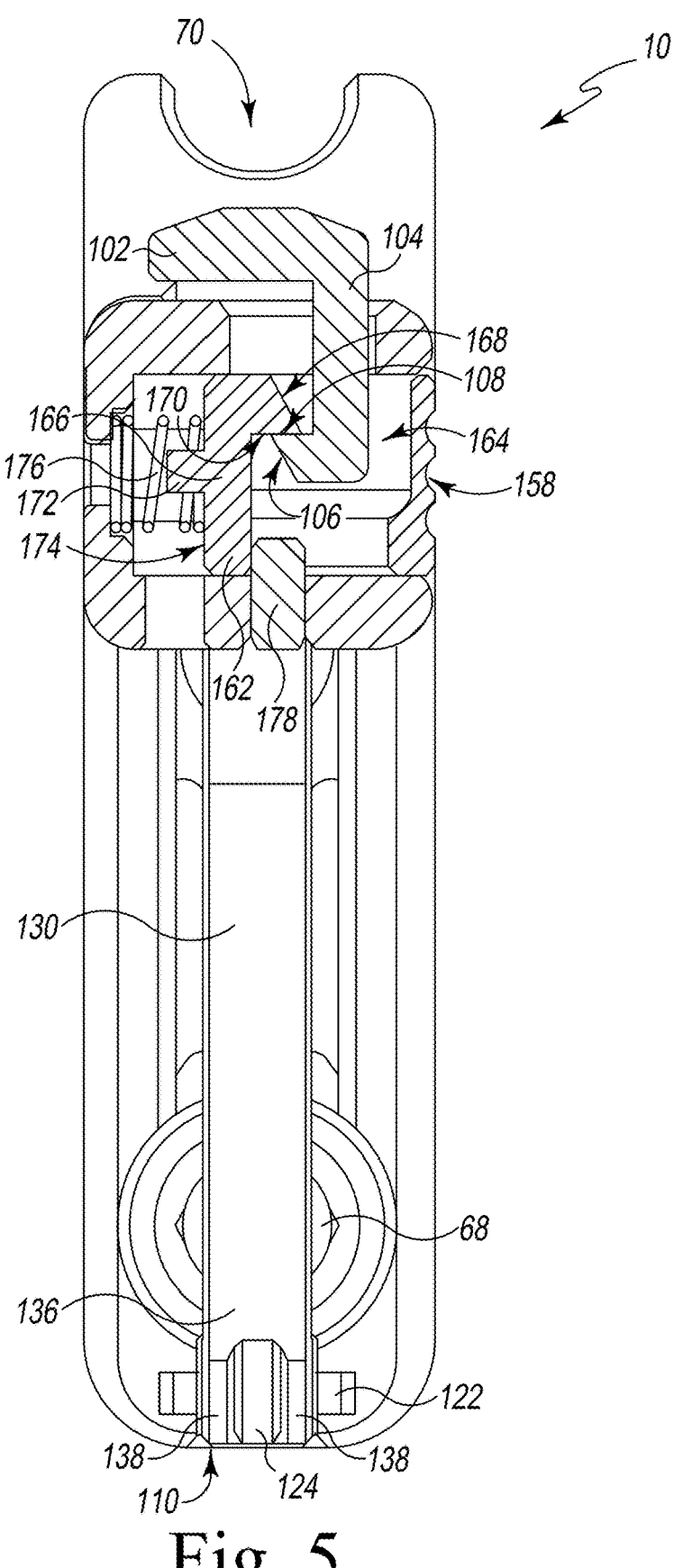
FIG. 5 is a cross-sectional rear elevation view of the offset acetabular shell impactor adapter of FIG. 3.

The body 96 of the latch lever 74 extends toward a latch end 102. The latch end 102 includes a latch 104 extending downward from the lever body 96. As shown in the cross-sectional view of FIG. 5, the latch 104 includes a lower cam surface 106 and an upper surface 108 extending inward toward the interior of the body 12. As described further below, when the lever 74 is in a latched position as shown in FIGS. 3-5, the latch 104 of the latch lever 74 may be captured within the body 12 by a pushbutton catch mechanism. In the latched position, the body 96 of the lever 74 may contact the top surface 30 of the body 12, operating as a stop that limits range of motion of the lever 74. As described above, the latch lever 74 is moveable between the open position as shown in FIGS. 1-2 and the latched position shown in FIGS. 3-5.

The body 12 further includes an aperture 110 defined in the bottom surface 32. The aperture 110 extends from the opening 40 toward the implant end 16. An inner wall 112 extends from the aperture 110 into the cavity 44. A groove 114 is defined in the inner wall 112 surrounding the aperture 110.

A bolt carrier 116 is positioned within the aperture 110. The bolt carrier 116 includes an upper surface 118 having a notch 120 defined thereon. As shown in FIGS. 2 and 4, the notch 120 is sized to receive the head 66 of the bolt 62. A rail 122 surrounds the sides and front of the carrier 116, and a tang 124 extends from the rear of the carrier 116. A bore 126 is defined through the tang 124. When the bolt carrier 116 is positioned in the aperture 110, the rail 122 is received in the groove 114 defined in the inner wall 112. The carrier 116 is slideable toward and away from the impactor end 14 when captured within the groove 114. Because the head 66 of the bolt 62 is captured by the carrier 116, when the carrier 116 slides toward the impactor end 14, the bolt 62 also slides in that same direction, thereby retracting the threaded body 64 of the bolt 62 into the body 12 through the circular aperture 54.

The impactor adapter 10 further includes a leaf spring 128 or other compliant connective member that connects the latch lever 74 and the bolt carrier 116. The leaf spring 128 includes a flexible body 130 that extends between ends 132, 134. The end 132 is pivotally coupled to the pivot end 76 of the latch 76, and the end 134 is pivotally coupled to the tang 124 of the carrier 116. Illustratively, each of the ends 132, 136 includes a fork 136 that extends to a pair of mounting plates 138. A circular opening 140 is defined through each mounting plate 138. The mounting plates 138 of the end 132 surround a bore 142 defined through the pivot end 76 of the lever. A pin 144 is positioned in the openings 140 and the bore 142 to pivotally couple the end 132 to the lever 74. Similarly, the mounting plates 138 of the end 134 surround the bore 126 defined through the carrier 116, and a pin 146 is positioned in the openings 140 and the bore 126 to pivotally couple the end 138 to the carrier 116.

When the lever 74 is in the open position (as shown in FIGS. 1-2), the leaf spring 128 has a relaxed, doubly arcuate shape. When the lever 74 is moved to the latched position (as shown in FIGS. 3-5), the leaf spring 128 has a relatively extended and flattened shape, causing the leaf spring 128 to be in tension. When in tension, the leaf spring 128 urges the carrier 116 to slide back in the groove 114 toward the impactor end 14. The carrier 116, in turn, pulls the slideable bolt 62 back toward the impactor end 14. Tension on the leaf spring 128 may be released by moving the lever 74 from the latched position to the open position as described further below.

As shown in FIGS. 1-5, an opening 148 is defined in the side surface 34 of the body 12. The opening 148 is positioned between the cavity 44 and the impactor end 14 on the straight segment 18 of the body 12. One or more inner walls 150 extend inwardly from the opening 148, defining a cavity 152. An additional opening 154 is defined in the top surface 30. A passageway extends through the opening 154 into the cavity 152.

A pushbutton catch 156, also referred to as a button 156, is positioned within the cavity 152. As described further below, the pushbutton catch 156 may be used to selectively retain the latch lever 74 in the latched position shown in FIGS. 3-5. The pushbutton catch 156 includes a button surface 158 positioned toward the side surface 34 of the body 12. The button surface 158 is configured to be pressed by a surgeon and thus may be textured or otherwise configured to provide additional grip. Additionally, as shown in FIG. 5, in ordinary operation the button surface 158 may be flush with the side surface 34 and/or recessed within the cavity 152 in order to prevent unintentional operation.

The pushbutton catch 156 further includes a pair of side walls 160 that extend inward from the button surface 158 into the cavity 152. The side walls are connected by a back wall 162. Together, the button surface 158, the side walls 160, and the back wall 162 surround a button cavity 164. A catch 166 extends upward from the back wall 162 and inward into the button cavity 164. The catch 166 includes an upper cam surface 168 and a lower surface 170. A guide pin 172 extends from a back surface 174 of the catch 166 toward the other side surface 36. A helical spring 176 is retained between the body 12 and the back surface 174 of the catch 166, and the guide pin 172 is captured within the spring 176. The spring 176 urges against the body 12 and the back surface 174 to bias the pushbutton catch 156 toward the opening 148 in the side surface 34. A stop pin 178 extending into the latch cavity 152 is positioned in a hole defined through the bottom surface 32 of the body 12. When the pushbutton catch 156 is positioned in the cavity 152, the stop pin 178 also extends into the button cavity 164. The stop pin 178 thus engages the back wall 162 of the pushbutton catch 156 and retains the pushbutton catch 156 within the cavity 152 of the body 12.

As shown in FIG. 5, when the lever 74 is in the latched position, the latch 104 extends into the cavity 152 and the button cavity 164. The upper surface 108 of the latch 104 engages the lower surface 170 of the catch 166, thereby retaining the latch 104 within the button cavity 164. When the surgeon or other user depresses the button surface 162, the pushbutton catch 156 slides toward the side surface 36, and the lower surface 170 of the catch 166 slides off the upper surface 108, releasing the latch 104. As described above, the spring 88 biases the latch lever 74 to the open position. Thus, when the latch 104 is released, the latch end 102 of the lever 74 automatically swings out of the cavity 152 toward the open position, which releases tension on the leaf spring 128.

When a surgeon or other user moves the lever 74 from the open position to the latched position without depressing the pushbutton catch 156, the lower cam surface 106 of the latch 104 engages the upper cam surface 168 of the catch 166. This engagement of the cam surfaces 110, 170 forces the pushbutton catch 156 to slide toward the side surface 36, allowing the latch 104 to enter the button cavity 164. When the latch 104 passes the catch 156 and the cam surfaces 110, 170 disengage, the spring 176 forces the pushbutton catch 156 to slide back toward the side surface 34, which causes the lower surface 170 of the catch 166 to retain the upper surface 108 of the latch 104. Accordingly, the latch lever 74 may be opened and/or closed by the surgeon using a single hand.

As shown in FIGS. 1-4, the impactor end 14 includes a shank 180, which is configured to be received by an automated surgical impactor. The illustrative shank 180 includes a pin 182 and a flange 184. The shank 180 is configured to be impacted by the automated surgical impactor in either a forward direction (i.e., to advance the impactor adaptor 10 toward the patient's bone) or a reverse direction (i.e., to back the impactor adaptor 10 out of the patient's bone). In other embodiments, it should be understood that the shank 180 may include any other configuration of pins, flanges, and/or other features configured to captured and/or impacted by the automated surgical impactor. The illustrative shank 180 further includes an indicator groove 186, which marks a depth at which the shank 180 is fully seated within the automated surgical impactor.

The body 12 further includes a round segment 188 positioned between the shank 180 and the pushbutton catch 156. The round segment 188 is configured as an attachment point for an inclination guide and/or a combined inclination and alignment guide. Additionally or alternatively, in some embodiments the body 12 may include one or more mounting brackets or other features configured to support attachment of additional orthopaedic surgical instruments.

Figure 6:
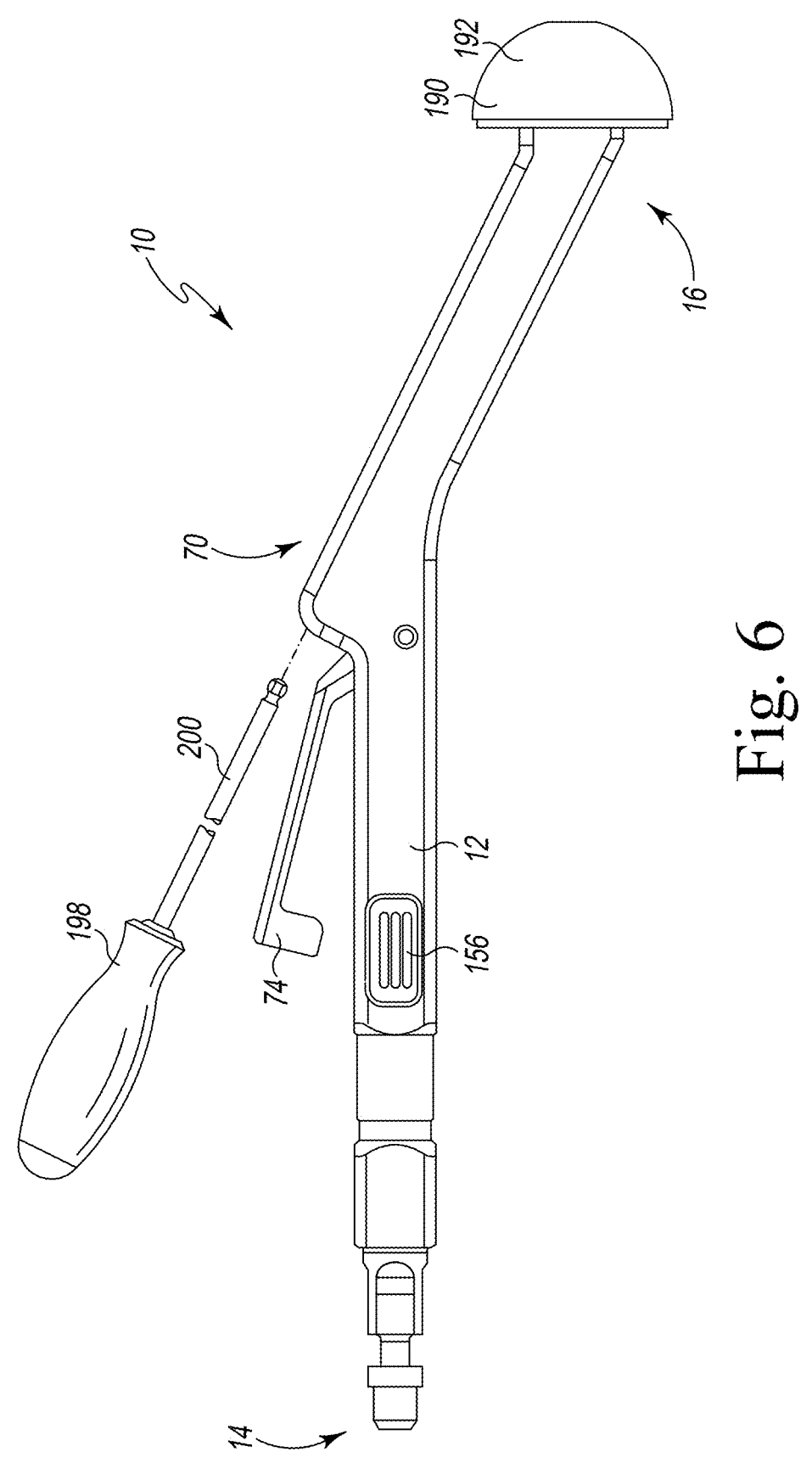
FIG. 6 is an elevation view of the offset acetabular shell impactor adapter of FIGS. 1-5 attached to an acetabular shell component and in the open configuration.
Figure 7:
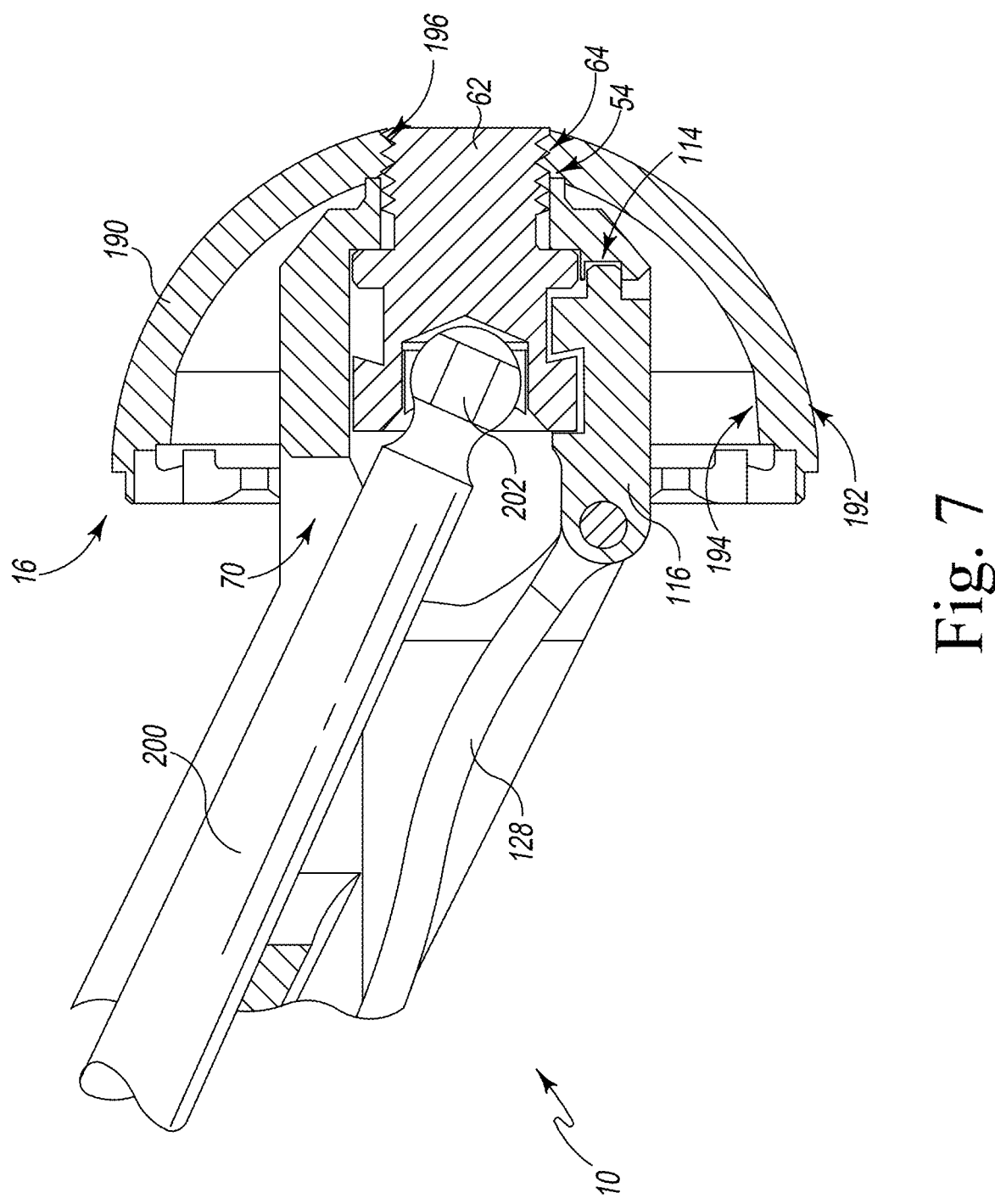
FIG. 7 is a fragmentary cross-sectional elevation view of the offset acetabular shell impactor and the acetabular shell component of FIG. 6.

The impactor adapter 10 may be utilized during the performance of an orthopaedic surgical procedure similar to that shown in FIGS. 6-10. Initially, the surgeon surgically prepares the patient's bone to receive an acetabular shell component. To do so, the surgeon may utilize a surgical reamer to prepare the patient's acetabulum to receive the shell component. After preparing the patient's bone, and as shown in FIGS. 6-7, the surgeon attaches an acetabular shell component 190 to the impactor adapter 10. The shell component 190 includes a domed outer surface 192 that is configured to be implanted in the patient's acetabulum. The outer surface 192 is illustratively semi-hemispherical, although in other embodiments the outer surface 192 may have any appropriate shape. The shell component 190 further includes an inner surface 194 positioned opposite the outer surface 192. A threaded central opening 196 is defined through the inner surface 194 and the outer surface 194.

As shown in FIG. 6, the lever 74 of the impactor adapter 10 is initially in the open position. When the lever 74 is in the open position, the leaf spring 128 urges the carrier 116 to slide forward toward the implant end 16 within the groove 114, which causes the threaded body 64 of the bolt 62 to extend outward through the circular aperture 54 defined in the convex surface 52 of the body 12. As shown in FIG. 7, the surgeon threads the threaded central opening 196 of the shell component 190 onto the threaded body 64 of the bolt 62, which extends outward from the implant end 16 of the body 12 as described above. The surgeon secures the shell component 190 to the implant adapter 10 by tightening the bolt 62 using a ball-end hex driver 198. As shown in FIGS. 6-7, the surgeon inserts a shaft 200 of the hex driver 198 through the guideway 70 formed by the upper surfaces 50 of the cross members 46, 48 and the inner walls 42 of the body 12. A tip 202 of the hex driver 198 contacts the head 66 of the bolt 62, allowing the surgeon to manually tighten the bolt 62. The surgeon may tighten the bolt 62 by hand until feeling a torque response or otherwise feeling resistance. The bolt 62 may not need to be fully tightened or otherwise tightened to any particular amount of torque.

After securing the shell component 190 to the impactor adapter 10, the surgeon removes the hex driver 198. The surgeon may rotate the shell component 190 about its central opening 196 in order to achieve a desired rotational position. As the bolt 62 is not fully tightened, the bolt 62 may also rotate with the shell component 190.

Figure 8:
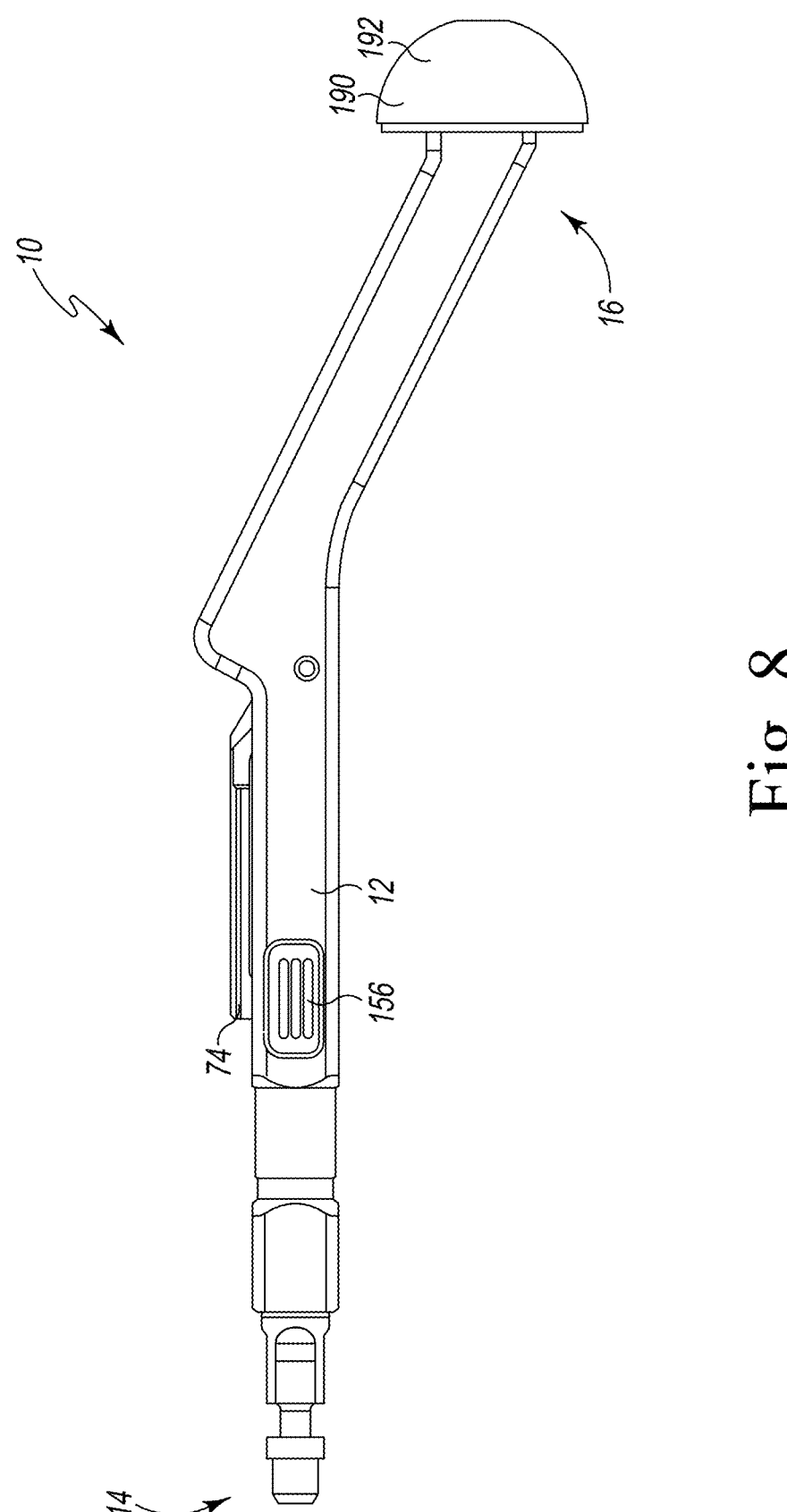
FIG. 8 is an elevation view of the offset acetabular shell impactor adapter of FIGS. 1-5 attached to the acetabular shell component and in the latched configuration.
Figure 9:
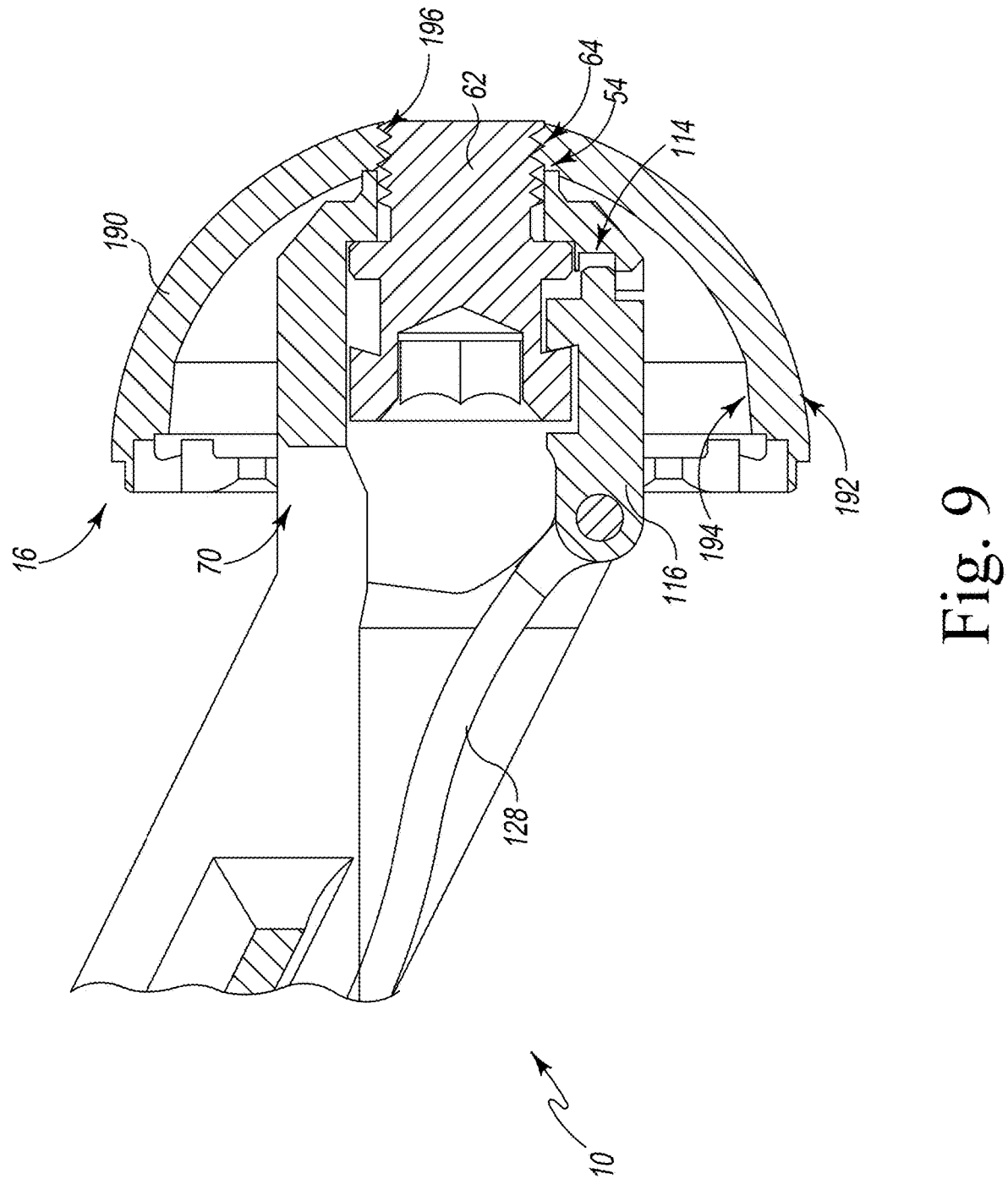
FIG. 9 is a fragmentary cross-sectional elevation view of the offset acetabular shell impactor and the acetabular shell component of FIG. 8.

After securing and optionally positioning the shell component 190, the surgeon moves the latch lever 74 from the open position to the latched position, as shown in FIGS. 8-9. As the latch lever 74 is moved to the latched position, the leaf spring 128 is extended and placed in tension. As the leaf spring 128 is placed in tension, the leaf spring 128 exerts a force on the carrier 116, pulling the carrier 116 back toward the impactor end 14. The carrier 116, in turn, exerts force on the bolt 62, which exerts force on the attached shell component 190. The force pulls the inner surface 194 of the shell component 190 fast against the boss 60 positioned on the implant end 16 of the body. The shell component 190 is thus held rigid and immobile against the implant adapter 10. As described above, when the latch lever 74 is in the latched position, the pushbutton catch 156 retains the latch 104, ensuring that the latch lever 74 remains in the latched position and that the shell component 190 remains rigidly attached to the impactor adaptor 10. Additionally, as the latch lever 74 is retained by the pushbutton catch 156, the leaf spring 128 is not extended to an over-center position in order to retain the latch lever 74. Thus, the impactor adapter 10 may have reduced wear and increased longevity as compared to impaction tools that use an over-center clamp function.

Figure 10:
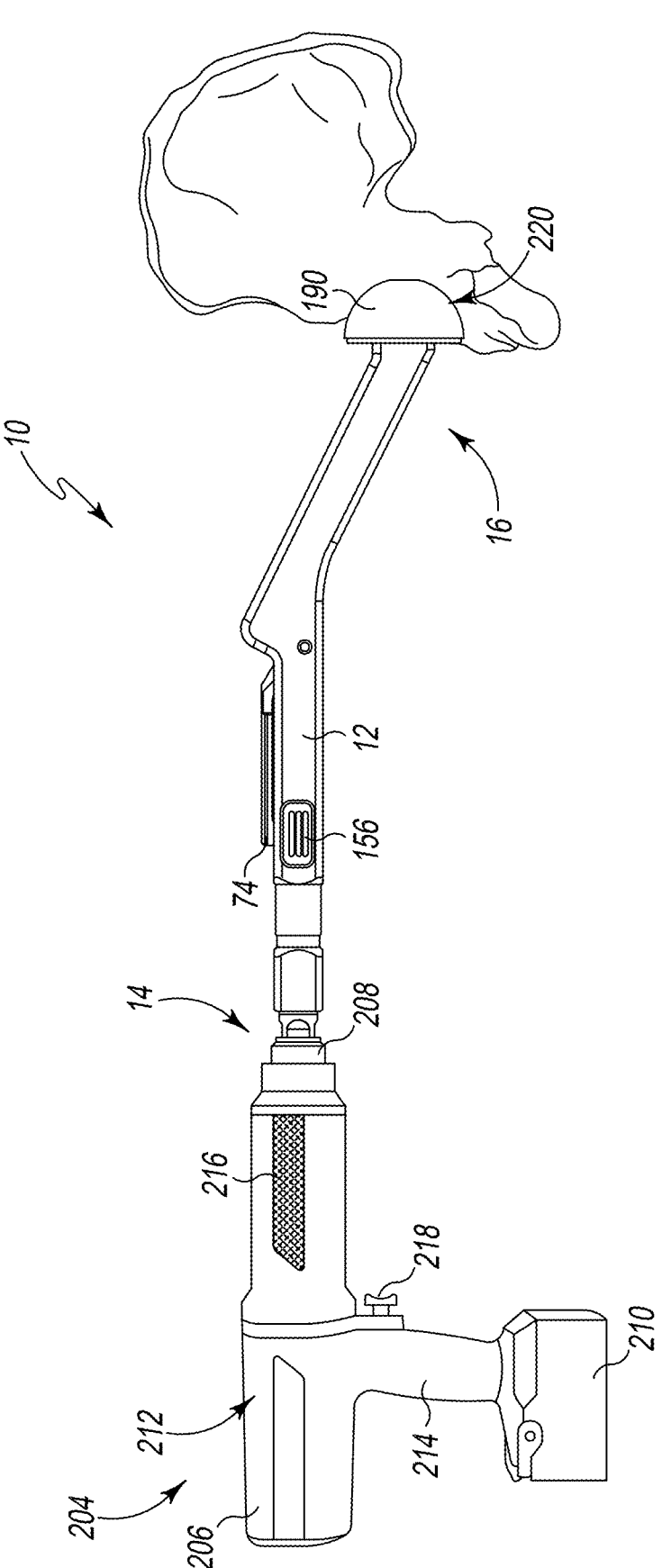
FIG. 10 is a perspective view of the offset acetabular shell impactor and the acetabular shell component during the performance of an orthopaedic surgical procedure using an automated surgical impactor.

After latching the impactor adapter 10, the surgeon or other user attaches the impactor end 14 of the impactor adapter 10 to an automated surgical impactor 204 as shown in FIG. 10. Additionally or alternatively, in some embodiments the impactor adapter 10 may be attached to the automated surgical impactor 204 before being attached to the shell component 190.

The automated surgical impactor 204 may be embodied as a Kincise™ surgical automated system component commercially available from DePuy Synthes of Warsaw, Indiana. In the illustrative embodiment, the automated surgical impactor 204 includes an impactor body 206 having a twist-lock collar 208 and a battery pack 210. Electrical drive components 212 are housed within the impactor body 206. The impactor body 206 further includes a primary hand grip 214, a secondary hand grip 216, and a trigger 218.

In use, the surgeon inserts the shank 180 of the impactor adapter 10 into the twist-lock collar 208 and then locks the collar 208 on to the shank 180. Holding the primary hand grip 214 and/or the secondary hand grip 216, the surgeon inserts the shell component 190 into the surgically prepared acetabulum 220 of the patient as shown in FIG. 10. After positioning the shell component 190, the surgeon depresses the trigger 218, which causes the electrical drive components 212 to generate a series of controlled percussive impacts on the impactor adapter 10 using electrical energy provided by the battery pack 208. The impactor adaptor 10 communicates impaction force from those percussive impacts to the shell component 190, thereby implanting the shell component 190 into the patient's acetabulum 220. During impaction, the surgeon's hands may remain on the automated surgical impactor 204, and the latch lever 74 remains in the latched position. Additionally, the leaf spring 128 retains the shell component 190 rigidly against the impactor adaptor 10 during impaction. Unlike adapters using a typical rigid drive train attachment mechanism, the compliant, flexible leaf spring 128 of the impactor adapter 10 may not back out or otherwise loosen during impaction, even when subject to frequent, lower-amplitude impactions generated by the automated surgical impactor 204.

After the shell component 190 has been fully impacted into the patient's acetabulum 220, the surgeon removes the impactor adaptor 10 from the shell component 190. To do so, the surgeon depresses the button surface 158 of the pushbutton catch 156, causing the pushbutton catch 156 to slide into the cavity 152 in the body 12. As the pushbutton catch 156 slides into the cavity 152, the lower surface 170 disengages the upper surface 108 of the latch 104, which releases the latch end 102 of the latch lever 74. The spring 88 causes the lever 74 to swing open to the open, unlatched position. In the open position, tension on the leaf spring 128 is released and the leaf spring 128 does not exert a force on the carrier 116 toward the impactor end 14. The carrier 116, in turn, stops exerting force on the bolt 62 toward the impactor end 14. Accordingly, the surgeon is able to unlatch the impactor adapter 10 with one hand.

After unlatching the impactor adaptor 10, the surgeon removes the shell component 190 from the threaded body 64 of the bolt 62. The surgeon inserts the hex driver 198 into the guideway 70 until the tip 202 of the hex driver 198 contacts the head 66 of the bolt 62. The surgeon uses the hex driver 198 to unthread the bolt 62 from the shell component 190. After the bolt 62 is unthreaded from the shell component 190, the surgeon removes the impactor adapter 10 from the shell component 190. After removing the impactor adapter 10, the shell component 190 remains in the patient's acetabulum 220, and the surgeon may proceed with implanting additional prosthetic components such as an acetabular bearing or liner. It should be understood that the surgeon may also remove the impactor adaptor 10 from the automated surgical impactor 204 before or after removing the shell component 190 from the impactor adaptor 10.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for performing an orthopaedic surgical procedure, the method comprising:

securing an acetabular shell component to a first end of an orthopaedic surgical instrument;

moving a lever of the orthopaedic surgical instrument from a first position to a second position in response to securing the acetabular shell component to the first end, wherein moving the lever from the first position to the second position comprises (i) pivoting a pivot end of the lever about an elongated body of the orthopaedic surgical instrument, (ii) latching a latch positioned on an opposite latch end of the lever to a pushbutton catch of the orthopaedic surgical instrument positioned in the elongated body so as to secure the lever in the second position, and (iii) applying tension with a leaf spring pivotally coupled to the lever on the acetabular shell component against the first end; and coupling a second end of the orthopaedic surgical instrument to an automated surgical impactor in response to moving the lever.

2. The method of claim 1, wherein securing the acetabular shell component to the first end comprises:

threading a central threaded hole of the acetabular shell component onto a threaded body of a slideable bolt of the orthopaedic surgical instrument, wherein the threaded body extends outward from the first end of the orthopaedic surgical instrument;

positioning a driver tool in a guideway defined by a top surface of the orthopaedic surgical instrument in response to threading the central threaded hole onto the threaded body; and tightening a head of the slideable bolt with the driver tool in response to positioning the driver tool.

3. The method of claim 1, further comprising:

adjusting a rotational position of the acetabular shell component in response to securing the acetabular shell component to the first end;

wherein moving the lever further comprises moving the lever in response to adjusting the rotational position.

4. The method of claim 1, further comprising:

impacting the acetabular shell component with the automated surgical impactor into a surgically prepared acetabulum of a patient in response to coupling the second end to the automated surgical impactor;

depressing the pushbutton catch of the orthopaedic surgical instrument in response to impacting the acetabular shell component, wherein depressing the pushbutton catch comprises unlatching the lever from the second position and releasing tension with the leaf spring; and releasing the acetabular shell component from the first end of the orthopaedic surgical instrument in response to depressing the pushbutton catch.

5. The method of claim 1, wherein moving the lever of the orthopaedic surgical instrument from the first position to the second position comprises contacting a top surface of the elongated body of the orthopaedic surgical instrument with a body of the lever;

wherein the pushbutton catch is positioned on a side surface of the elongated body that extends away from the top surface of the elongated body.

6. The method of claim 1, wherein pivoting the pivot end of the lever about the elongated body of the orthopaedic surgical instrument comprises compressing a helical spring between the pivot end of the lever and a portion of the elongated body.

* * * * *